US011512030B2

(12) United States Patent
Peitz et al.

(10) Patent No.: US 11,512,030 B2
(45) Date of Patent: Nov. 29, 2022

(54) PROCESS FOR OLIGOMERIZATION OF ISOBUTENE

(71) Applicant: Evonik Operations GmbH, Essen (DE)

(72) Inventors: Stephan Peitz, Oer-Erkenschwick (DE); Guido Stochniol, Haltern am See (DE); Johannes Knossalla, Gahlen (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/463,604

(22) Filed: Sep. 1, 2021

(65) Prior Publication Data

US 2022/0073438 A1 Mar. 10, 2022

(30) Foreign Application Priority Data

Sep. 4, 2020 (EP) ..................................... 20194598

(51) Int. Cl.
*C07C 2/28* (2006.01)
*C07C 7/04* (2006.01)

(52) U.S. Cl.
CPC .................. *C07C 2/28* (2013.01); *C07C 7/04* (2013.01); *C07C 2531/08* (2013.01)

(58) Field of Classification Search
CPC ......... C07C 2/28; C07C 7/04; C07C 2531/08; C07C 2/08
See application file for complete search history.

(56) References Cited

U.S. PATENT DOCUMENTS

| 4,100,220 A * | 7/1978 | Bowman ................. C07C 29/04 585/824 |
| 6,613,108 B1 * | 9/2003 | Aittamaa .................. C07C 9/21 585/521 |
| 9,688,590 B2 * | 6/2017 | Cross, Jr. ................. C10G 3/42 |
| 2004/0181106 A1 * | 9/2004 | Nurminen ................. C07C 2/12 585/533 |
| 2005/0137435 A1 * | 6/2005 | Tiitta .................... C07C 5/2518 585/329 |
| 2011/0230690 A1 * | 9/2011 | Tiita ......................... C07C 9/21 585/510 |
| 2014/0128562 A1 | 5/2014 | Kobayashi |
| 2015/0344383 A1 * | 12/2015 | Subramani .......... B01J 35/1014 585/510 |

FOREIGN PATENT DOCUMENTS

| GB | 959 756 | 6/1964 |
| WO | 01/51435 | 7/2001 |

OTHER PUBLICATIONS

European Search Report dated Feb. 18, 2021 in European Patent Application No. 20194598.7, 5 pages.

\* cited by examiner

*Primary Examiner* — Ali Z Fadhel
(74) *Attorney, Agent, or Firm* — Grüneberg and Myers, PLLC

(57) ABSTRACT

A process can be used for oligomerization of isobutene by conversion of an isobutene-containing hydrocarbon stream over an acid catalyst in at least one reaction stage, where a particular ratio of recycle to feed is employed.

20 Claims, 4 Drawing Sheets

PROCESS FOR OLIGOMERIZATION OF ISOBUTENE

CROSS-REFERENCE TO RELATED APPLICATIONS

This application claims priority to European Patent Application No. 20194598.7, filed on Sep. 4, 2020, the content of which is hereby incorporated by reference in its entirety.

BACKGROUND OF THE INVENTION

Field of the Invention

The present invention relates to a process for oligomerization of isobutene by conversion of an isobutene-containing hydrocarbon stream over an acid catalyst in at least one reaction stage, wherein a particular ratio of recycle to feed is employed.

Description of Related Art

The oligomerization of isobutene is a known large industrial scale process for producing diisobutene. Diisobutene is an industrial designation for a mixture of 2,4,4-trimethylpent-1-ene and 2,4,4-trimethylpent-2-ene which is employed in the synthesis, for example hydroformylation to afford the aldehyde, or after hydrogenation as a fuel component. Known measures for technical improvement of this process have already been described for example in EP 1 388 528 A1.

Despite the known processes there is a continuous need for process improvement, in particular in respect of selectivity for 2,4,4-trimethylpent-1-ene. This is because it is advantageous for the hydroformylation of diisobutene when the diisobutene comprises predominantly 2,4,4-trimethylpent-1-ene. It has now been found that, surprisingly, the selectivity for 2,4,4-trimethylpent-1-ene may be enhanced according to the recycle-to-feed ratio.

SUMMARY OF THE INVENTION

The underlying object of the present invention which was that of providing an improved process for oligomerization of isobutene with a higher selectivity for 2,4,4-trimethylpent-1-ene in the diisobutene formed has been solved by the process as described. Preferred embodiments of the process are also described below.

The invention also includes the following embodiments:
1. Process for producing diisobutene by oligomerization of isobutene over an acid catalyst in at least one reaction stage which in each case contains at least one reactor and at least one distillation column, wherein
   an isobutene-containing input stream which comprises an isobutene-containing hydrocarbon stream as feed and a recirculated stream as recycle is converted in the at least one reactor of the at least one reaction stage to obtain a product mixture containing at least the diisobutene formed having a proportion of 2,4,4-trimethylpent-1-ene of at least 75 mol %, preferably at least 76.5 vol %, particularly preferably at least 78 mol %, and unconverted isobutene, and the obtained product mixture is supplied to the at least one distillation column,
   at the top of the distillation column a residual hydrocarbon stream depleted in the diisobutene formed based on the obtained product mixture is withdrawn and at least partially recirculated to the at least one reactor as recycle, characterized in that the ratio of recycle to feed is at least 4.
2. Process according to embodiment 1, wherein the ratio or recycle to reed is at least 5.
3. Process according to embodiment 2, wherein the ratio of recycle to feed is at least 8.
4. Process according to any of embodiments 1 to 3, wherein the isobutene-containing hydrocarbon stream is a $C_4$-hydrocarbon stream.
5. Process according to any of embodiments 1 to 3, wherein the isobutene-containing hydrocarbon stream is a pure isobutene stream.
6. Process according to any of embodiments 1 to 5, wherein the residual hydrocarbon stream withdrawn at the top of the column is completely recirculated to the at least one reactor.
7. Process according to any of embodiments 1 to 6, wherein a reaction stage comprises at least two reactors which are connected in series or parallel relative to one another.
8. Process according to any of embodiments 1 to 7, wherein the oligomerization is performed in the liquid phase.
9. Process according to any of embodiments 1 to 8, wherein the acid catalyst is an acidic ion exchange resin in which a portion of the acidic protons have been exchanged for metal ions.
10. Process according to embodiment 9, wherein 0.1% to 70% of the acidic protons, preferably 30% to 65% of the acidic protons, of the ion exchanger have been exchanged for metal ions.
11. Process according to embodiment 9 or 10, wherein the metal ions are ions of the alkali metals, alkaline earth metals and/or rare earths.
12. Process according to any of embodiments 1 to 11, wherein the reactor is a flow reactor, for example a fixed bed reactor, a tube bundle reactor, a continuous stirred tank reactor or a loop reactor.
13. Process according to any of embodiments 1 to 12, characterized in that the at least one reactor employed in the process is operated adiabatically, polytropically or virtually isothermally using a coolant.
14. Process according to any of embodiments 1 to 13, wherein the oligomerization is performed at a temperature between 5° C. and 160° C., particularly preferably between 30° C. and 110° C., very particularly preferably between 40° C. and 90° C.
15. Process according to any of embodiments 1 to 14, wherein the first reaction stage is run with a total feed of the isobutene-containing input stream of at least 2.5 t per t of catalyst and hour (h) (unit t/(t*h)), preferably at least 3 t/(t*h) and particularly preferably at least 3.5 t/(t*h).

DETAILED DESCRIPTION OF THE INVENTION

Figure 1:
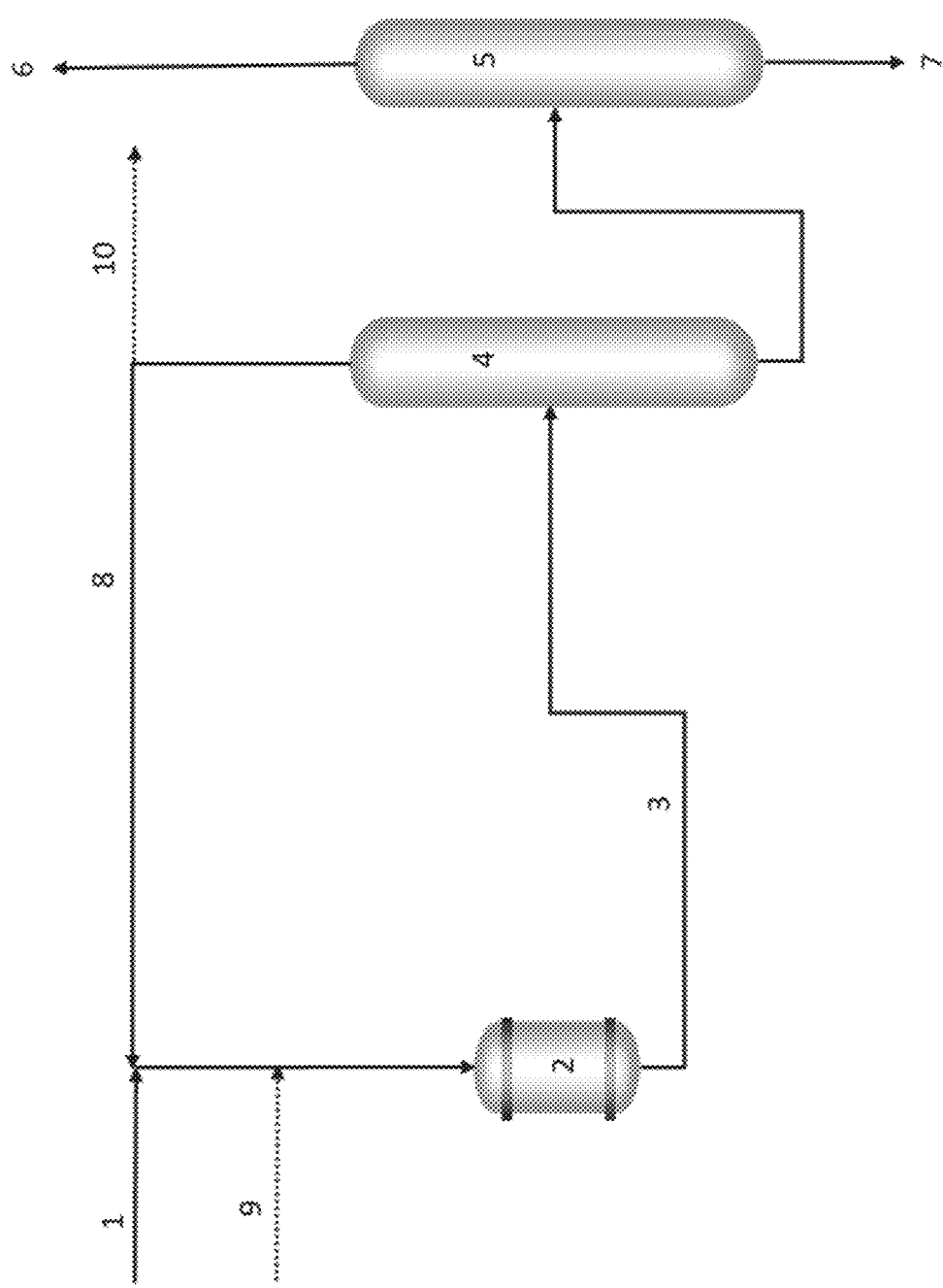
FIG. 1 shows an embodiment of the process according to the invention having a reactor (2) in a reaction stage with two distillation columns (4, 5).

The process according to the invention is accordingly a process for producing diisobutene by oligomerization of isobutene over an acid catalyst in at least one reaction stage which in each case comprises at least one reactor and at least one distillation column, wherein an isobutene-containing input stream which comprises an isobutene-containing hydrocarbon stream as feed and a recirculated stream as recycle is converted in the at least one reactor of the at least one reaction stage to obtain a product mixture containing at least the diisobutene formed having a proportion of 2,4,4-trimethylpent-1-ene of at least 75 mol %, preferably at least 76.5 vol %, particularly preferably at least 78 mol %, and unconverted isobutene, and the obtained product mixture is supplied to the at least one distillation column, at the top of the distillation column a residual hydrocarbon stream depleted in the diisobutene formed based on the obtained product mixture is withdrawn and at least partially recirculated to the at least one reactor as recycle, wherein the ratio of recycle to feed is at least 4.

It has surprisingly been found that the selectivity of the oligomerization reaction for 2,4,4-trimethylpent-1-ene can be increased as a result of the ratio of recycle to feed in the isobutene-containing input stream of at least 4. The ratio of recycle to feed is preferably at least 5, particularly preferably at least 6. This makes it possible to achieve even better selectivities for 2,4,4-trimethylpent-1-ene.

The isobutene-containing input stream employed in the inventive oligomerization of isobutene to produce diisobutene in the first reactor and—if present—in every reactor of every reaction stage present connected in parallel relative to the first reactor comprises both an isobutene-containing hydrocarbon stream as feed (fresh feed) and a stream recirculated from the distillation downstream of the oligomerization as recycle. This employed isobutene-containing input stream preferably consists of an isobutene-containing hydrocarbon stream as feed (fresh feed), a recirculated stream as recycle and optionally a dilution stream composed of inert alkanes. If, in the process according to the invention, one or more serially connected reactors are present for the first reactor of each reaction stage present, these are fed only with the discharge from the preceding reactor without additionally supplying the recycle.

The employed isobutene-containing stream employed as feed in the process according to the invention may in principle be any isobutene-containing hydrocarbon mixtures comprising isobutene in an amount which makes it possible to achieve economic operation of the process. It is preferable to employ mixtures of isobutene and further C4-hydrocarbons, i.e. C4-hydrocarbon streams. In the context of the present invention, the discharge from a preceding oligomerization reactor is also considered as isobutene-containing stream. Industrial mixtures which contain isobutene are for example light petroleum fractions from refineries, C4-fractions from crackers (for example steamcrackers, hydrocrackers, catcrackers), mixtures from Fischer-Tropsch syntheses, mixtures from the dehydrogenation of butanes, mixtures from the skeletal isomerization of linear butenes and mixtures obtained by metathesis of olefins.

In a particularly preferred embodiment of the present invention, a pure isobutene stream is employed as the isobutene-containing hydrocarbon stream, i.e. as feed. In this context the term "pure" is to be understood as meaning that a pure isobutene stream contains at least 98% by weight of isobutene based on the total mass of the stream. The isobutene concentration at the entrance to the first reaction stage/the first reactor of the first reaction stage, i.e. the isobutene concentration in the employed isobutene-containing input stream, shall preferably not exceed 90%, more preferably 87%, particularly preferably 85%.

In order to limit the isobutene concentration to limit a temperature increase in the reactor, the isobutene-containing hydrocarbon stream may be admixed with a defined amount of a solvent or diluent. Suitable solvents or diluents include inert substances such as alkanes, preferably isobutane.

The total feed of the isobutene-containing input stream of the first reaction stage/the first reactor of the first reaction stage may be varied within wide ranges. This is dependent on the actual construction (one or more reactors, etc.) and the size of reactor(s) and distillation column(s). In a preferred embodiment of the present invention, the first reaction stage/the first reactor of the first reaction stage or al serially connected reactors of the first reaction stage are run with a total feed of the isobutene-containing input stream of at least 2.5 t per t of catalyst and hour (h) (unit t/(t*h)), preferably at least 3 t/(t*h) and particularly preferably at least 3.5 t/(t*h). The total feed is the amount of feed based on the mass of the present catalyst per unit time (hour). This is always based on the total catalyst mass of reactors connected in series. If only one reactor is present, the catalyst mass is the mass of the catalyst in the one reactor. If two or more reactors connected in series are present, the catalyst mass is the sum total of the catalyst masses from the two or more reactors connected in series.

The oligomerization of isobutene according to the invention is performed in at least one reaction stage. It may be advantageous to use two or more reaction stages, but for the oligomerization of isobutene according to the invention it is preferred when only one reaction stage is present. This is easier to realize in terms of plant engineering and is potentially less costly.

In the context of the present invention, one reaction stage comprises at least one reactor and at least one distillation column. Two more reactors and/or two or more distillation columns may also be present. If more than one reaction stage is present, the number of reactors and/or distillation columns in al reaction stages may be identical or different. In the present case it is preferable when one reaction stage comprises at least two reactors which are connected in series or parallel relative to one another. If the two reactors are connected in parallel, both reactors are supplied with fresh feed and recycle in the ratio according to the invention in each case. If the reactors are arranged in series, the second reactor is supplied with the product mixture from the first reactor.

According to the invention, the oligomerization of isobutene may be performed batchwise or preferably continuously. Suitable reactors for the continuous process mode include flow reactors, for example fixed bed reactors, tube bundle reactors, continuous stirred tank reactors, loop reactors or a combination thereof. For the batchwise process mode, stirred tank reactors are suitable. The reactors employed in the present process may be operated adiabatically, polytropically or virtually isothermally, i.e. using a coolant with which the reactor is cooled. Virtually isothermal is to be understood as meaning that the temperature at any point in the reactor is not more than 15 K higher than the temperature at the reactor entrance.

The oligomerization of isobutene is effected by contacting the isobutene-containing input stream with an acid catalyst. The temperature during oligomerization is preferably between 5° C. and 160° C., particularly preferably between 30° C. and 110° C. very particularly preferably between 40° C. and 90° C.

The oligomerization according to the invention may further be performed at a pressure identical to or above the vapor pressure of the input stream at the respective reaction temperature, preferably at a pressure below 40 bar. The isobutene-containing input stream should be fully or partially in the liquid phase during the oligomerization. In a preferred embodiment of the present invention, the oligomerization is carried out in the liquid phase. The pressures and temperatures needed to obtain a liquid phase reaction are known to those skilled in the art and may be established on the basis of the abovementioned ranges.

The catalyst employed in the oligomerization of isobutene is an acid catalyst. Typical acid catalysts for oligomerization of isobutene to diisobutene are known to those skilled in the art. In a preferred embodiment, the employed acid catalyst is an acidic ion exchange resin in which a portion of the acidic protons have been exchanged for metal ions.

In the oligomerization according to the invention it is further preferable to employ solid sulfonated ion exchange resins in which especially 0.1% to 70% of the acidic protons, preferably 30% to 65% of the acidic protons of the sulfonic acid groups have been exchanged for metal ions. Suitable metal ions replacing the protons include ions of alkali metals, alkaline earth metals, chromium, manganese, iron, cobalt, nickel, zinc and aluminum and ions of the lanthanide group (rare earth). Preferably employed therefor are alkali metal ions, in particular sodium ions. It is also possible for the exchange to be performed with two or more different metal ions.

Suitable ion exchange resins are for example those produced by sulfonation of phenol/aldehyde condensates or of cooligomers of aromatic vinyl compounds. Examples of aromatic vinyl compounds for producing the cooligomers are styrene, vinyltoluene, vinylnaphthalene, vinylethylbenzene, methylstyrene, vinylchlorobenzene, vinylxylene and divinylbenzene. Especially cooligomers formed by reaction of styrene with divinylbenzene are used as precursors for the production of the sulfonated ion exchange resins preferred here. The properties of these resins, in particular specific surface area, porosity, stability, swelling/shrinkage and exchange capacity may be varied via the production process. These resins may be produced in gel-like, macroporous or sponge-like form.

The particle size of the ion exchange resin employed as acid catalyst according to the invention is preferably between 500 μm and 1500 μm, by preference between 600 μm and 1000 μm. Determination of particle size may be effected by laser light diffraction according to ISO 13320: 2020-01. The particle size distribution may be made relatively narrow or relatively broad, it is thus possible to employ ion exchange resins having a very uniform particle size (monodisperse resins). However, it is also possible to employ ion exchange resins present in the form of shaped bodies, for example cylinders, rings or spheres. If the process according to the invention employs two or more reactors these may be filled with ion exchange resins of identical or different particle size/with identical or different particle size distribution or in the form of different shaped bodies.

The ion exchange resins preferred according to the invention may be produced by various processes known to those skilled in the art. If the ion exchange resin is in the H-form, protons may be exchanged for metal ions. If the resin is in the form of a metal salt, metal ions may be replaced by protons using acids. This ion exchange may in principle be effected in either organic or aqueous suspension. One simple process is that of slurrying the ion exchange resin in the $H^+$ form with sufficient liquid (about one to ten times the intrinsic volume of the ion exchange resin) to produce a stirrable suspension. A solution containing the desired ions is then added to this suspension. Ion exchange is preferably effected in the temperature range from 10° C. to 100° C., particularly preferably 20° C. to 40° C. Once ion exchange is complete, the ion exchange resin is washed and dried. Drying may be effected under vacuum or in an inert gas stream, for example in a nitrogen stream. Drying temperatures are typically between 10° C. and 120° C.

A preferred route to producing the catalysts used in the process according to the invention is exchange of protons for metal ions in the aqueous phase, washing of the partially exchanged ion exchange resin with water and subsequent drying.

The ions with which the resin is to be laden may be in the form of solutions of hydroxides or salts of organic or inorganic acids. In the case of salts of polybasic acids, acidic salts may also be employed. It is likewise possible to employ compounds having other organic radicals such as for example alkoxides or acetylacetonates. Preferably employed as the source of the metal ions are metal hydroxides and salt of inorganic acids. It is very particularly preferable to employ alkali metal hydroxides, for example sodium hydroxide, alkali metal halides, for example sodium chloride, alkali metal sulfates, for example sodium sulfate, alkali metal nitrates, for example sodium nitrate, alkaline earth metal hydroxides and alkaline earth metal nitrates.

The approach described hereinabove makes it possible to produce catalysts of different activity and selectivity depending on extent of exchange, ion type and resin.

A reactor in the process according to the invention may contain a mixture of resins of different reactivities. It is likewise possible for a reactor to contain catalysts of different activities arranged in layers. If more than one reactor is used, the individual reactors may be filled with catalysts of identical or different activities.

The oligomerization according to the invention affords in the at least one reactor a product mixture containing at least the diisobutene formed having a proportion of 2,4,4-trimethylpent-1-ene of at least 75 mol %, preferably at least 78.5 mol %, particularly preferably at least 78 mol %, and unconverted isobutene. The product mixture may also contain isobutane.

The product mixture is subsequently supplied to the at least one distillation column of the reaction stage to separate the products of low boilers. The distillation is performed such that at least the low boilers, i.e. unconverted isobutene and—if present—isobutane are withdrawn as residual hydrocarbon stream at the top of the at least one distillation column. This residual hydrocarbon stream is partially or completely recirculated to the at least one reactor as recycle. Complete recirculation of the residual hydrocarbon stream from the at least one distillation column makes it possible to achieve a 100% conversion of isobutene. Accordingly the mass of isobutene in the isobutene-containing hydrocarbon stream supplied to the at least one reactor is only equal to the mass of product obtained in the sump of the at least one distillation column.

The distillation in the at least one distillation column is preferably performed at a pressure between 2 and 9 bar(g)

(bar gauge), preferably between 3 and 8 bar(g), particularly between 4 and 7 bar(g). The temperature during distillation in the sump of the column is preferably 100° C. to 220° C., more preferably 120° C. to 210° C., particularly preferably 150° C. to 200° C. in a particularly preferred embodiment of the present invention, the distillation in the at least one distillation column is operated with reflux (portion of total distillate stream (vapours) returned to the top of the column). The reflux ratio (ratio of vapours to reflux) is preferably 0.001 to 2, more preferably 0.005 to 1.5, and particularly preferably 0.01 to 1.

A mixture of the oligomers formed is obtained in the sump of the distillation column, wherein the mixture obtained in the sump comprises preferably at least 80% by weight of diisobutene, particularly preferably at least 88% by weight of diisobutene, very particularly preferably at least 92% by weight of diisobutene. A portion of the mixture may be triisobutenes or higher oligomers, but especially triisobutenes.

In a particularly preferred embodiment, the reaction stage for the process according to the invention comprises at least two distillation columns preferably connected in series. In the preferred series connection, the second distillation column is fed from the sump of the first distillation column. The second distillation column may be used to separate the mixture of the formed oligomers obtained in the first distillation to separate the diisobutene from any higher oligomers present, for example triisobutene.

To this end the pressure in the second distillation column is preferably set to 0.1 to 5 bar(a) (bar absolute), more preferably to 0.2 to 3 bar(a) and particularly preferably to 0.3 to 1.5 bar(a). The temperature in the sump of the second distillation column is preferably 30° C. to 180° C., more preferably 45° C. to 170° C. and particularly preferably 60° C. to 160° C. The reflux ratio in the second distillation column is preferably 0 to 2, more preferably 0.01 to 1.8 and particularly preferably 0.05 to 1.5.

The present invention is hereinbelow elucidated with reference to FIGS. 1 to 4. It is noted that these figures represent specific embodiments and serve the purpose of explanation without effecting any limitation to the subject matter of the invention.

FIG. 1 shows one embodiment of the process according to the invention comprising a reactor (2) in a reaction stage with two distillation columns (4, 5). An isobutene-containing input stream composed of an isobutene-containing hydrocarbon stream (feed) (1) and a stream (recycle) (8) recirculated from the first distillation column (4) is passed to the reactor (2) for oligomerization of the isobutene present. According to the invention, the ratio of recycle to feed in the isobutene-containing input stream is at least 4, preferably at least 5, particularly preferably at least 8. In the first distillation column (4), the discharge (3) from the reactor (2), which is a mixture of at least unconverted isobutene and isobutene oligomers, is freed of low boilers (isobutene and optionally isobutane) which are withdrawn from the top of the distillation column (4) and recirculated to the reactor (2). The sump product from the distillation column (4) consists substantially of diisobutene and higher oligomers which are separated from one another in the subsequent distillation column (5). The diisobutene (6) is obtained from the column top and the higher oligomers (7) accumulate in the sump. The figure indicates two optional configurations, namely additional supply of inert alkanes (9) and discharging of a portion of the low boilers (10).

Figure 2:
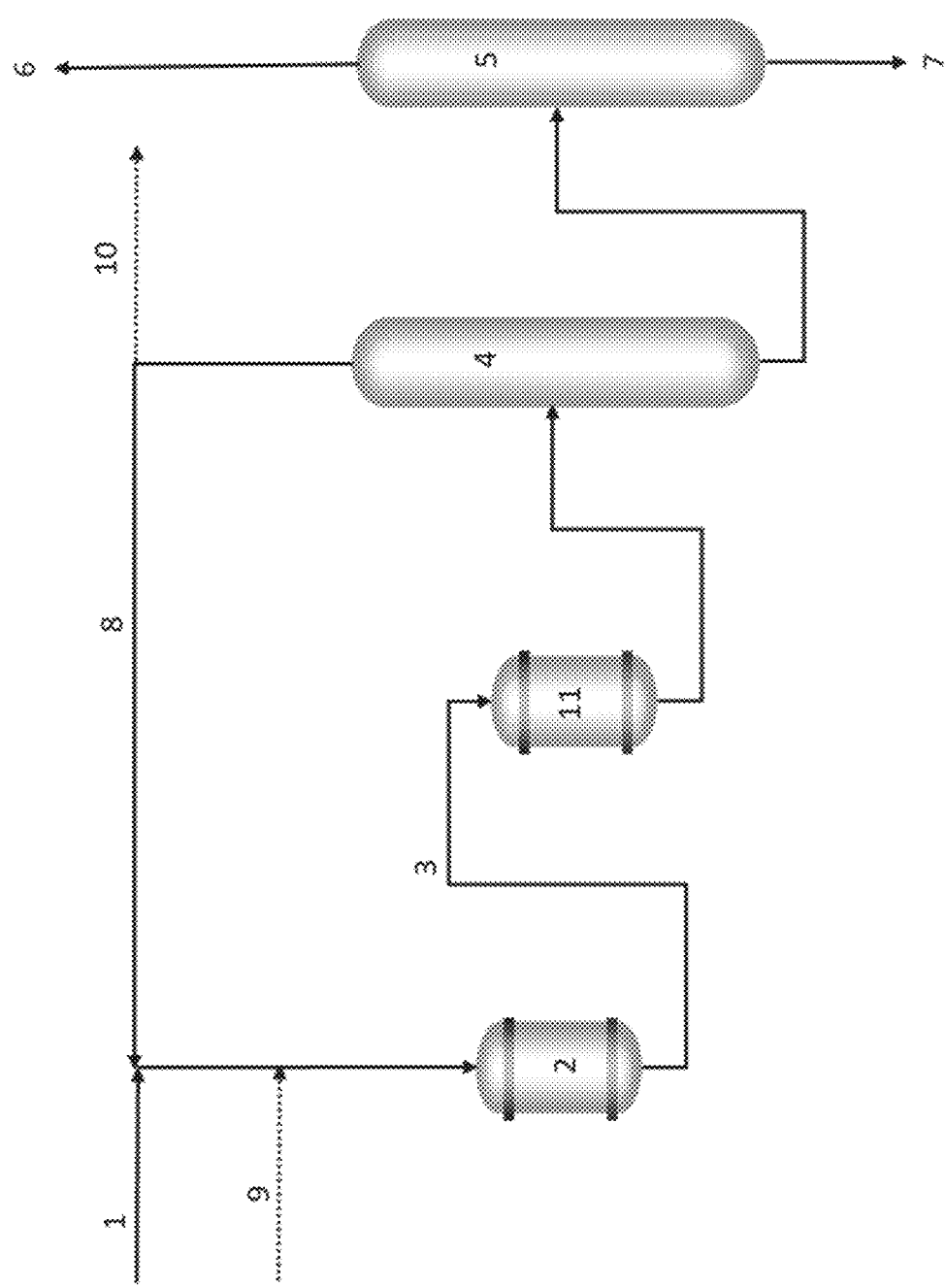
FIG. 2 shows an embodiment of the process according to the invention having two reactors (2, 11) connected in series.

In contrast to FIG. 1, the embodiment shown in FIG. 2 comprises two reactors (2, 11) connected in series. An isobutene-containing input stream composed of an isobutene-containing hydrocarbon stream (feed) (1) and a stream (recycle) (8) recirculated from the first distillation column (4) is passed to the first reactor (2) for oligomerization of the isobutene present. According to the invention, the ratio of recycle to feed in the isobutene-containing input stream is at least 4, preferably at least 5, particularly preferably at least 6. The discharge (3) from the first reactor (2), which is a mixture of at least unconverted isobutenes and isobutene oligomers, is then passed to a second reactor (11) to oligomerize the remaining isobutene. In the first distillation column (4), the discharge from the second reactor is then freed of low boilers (isobutene and optionally isobutane) which are withdrawn from the top of the distillation column (4) and recirculated to the first reactor (2). The sump product from the distillation column (4) consists substantially of diisobutene and higher oligomers which are separated from one another in the subsequent distillation column (5). The diisobutene (6) is obtained from the column top and the higher oligomers (7) accumulate in the sump. The figure also indicates two optional configurations, namely additional supply of inert alkanes (9) and discharging of a portion of the low boilers (10).

Figure 3:
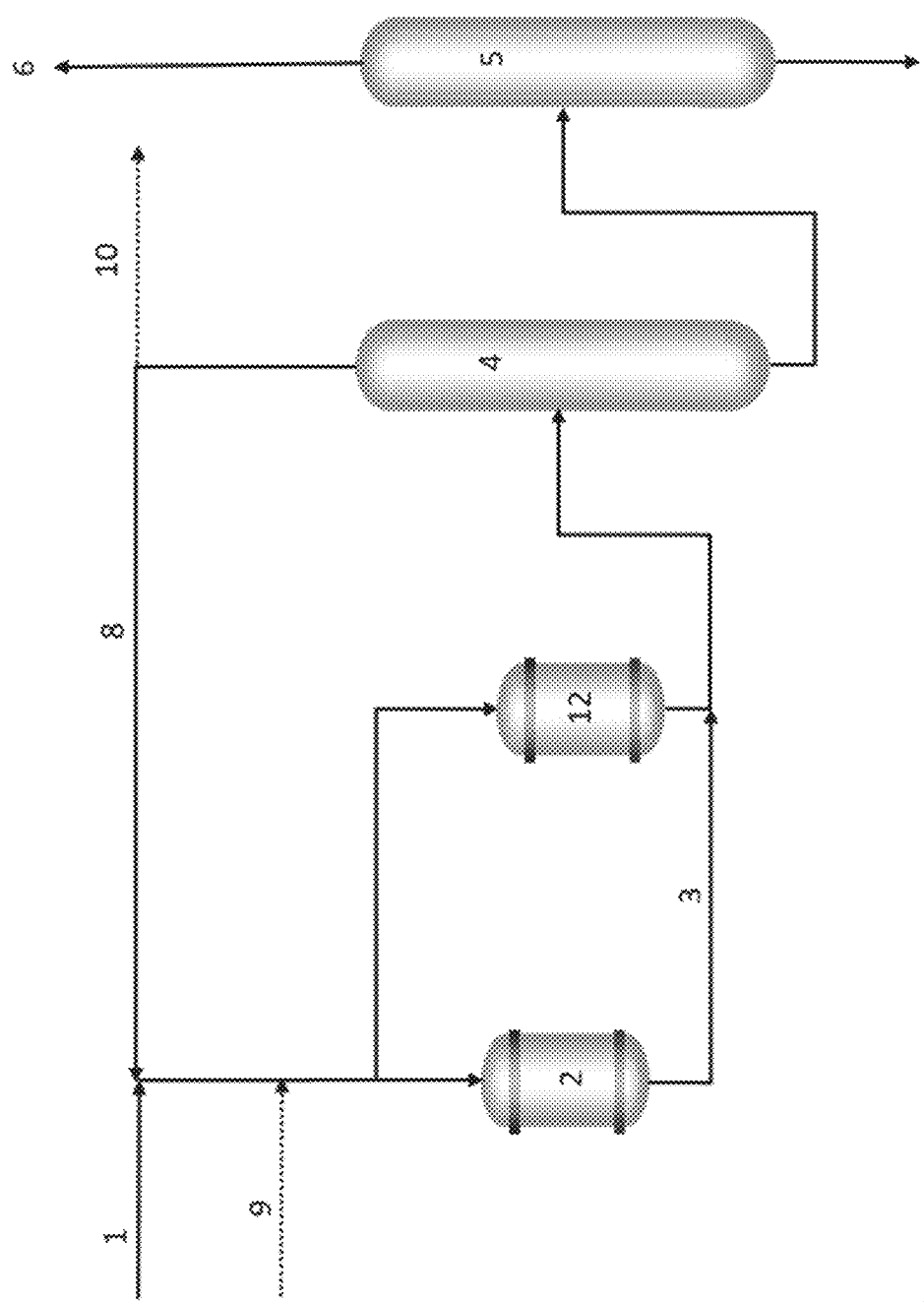
FIG. 3 shows an embodiment of the process according to the invention having two reactors (2, 12) connected in parallel.

The embodiment according to FIG. 3 likewise comprises two reactors (2, 12), but these are connected in parallel. An isobutene-containing input stream composed of an isobutene-containing hydrocarbon stream (feed) (1) and a stream (recycle) (8) recirculated from the first distillation column (4) is passed to the first reactor (2) and to the second reactor (12) for oligomerization of the isobutene present. According to the invention, the ratio of recycle to feed in the isobutene-containing input stream is at least 4, preferably at least 5, particularly preferably at least 6. In the first distillation column (4), the discharge (3) from the first reactor (2) and the discharge from the second reactor (12), which are in each case a mixture of at least unconverted isobutene and isobutene oligomers, are then freed of low boilers (isobutene and optionally isobutane) which are withdrawn from the top of the distillation column (4) and recirculated to the first and the second reactor (2, 12). The sump product from the distillation column (4) consists substantially of diisobutene and higher oligomers which are separated from one another in the subsequent distillation column (5). The diisobutene (6) is obtained from the column top and the higher oligomers (7) accumulate in the sump. The figure also indicates two optional configurations, namely additional supply of inert alkanes (9) and discharging of a portion of the low boilers (10).

Figure 4:
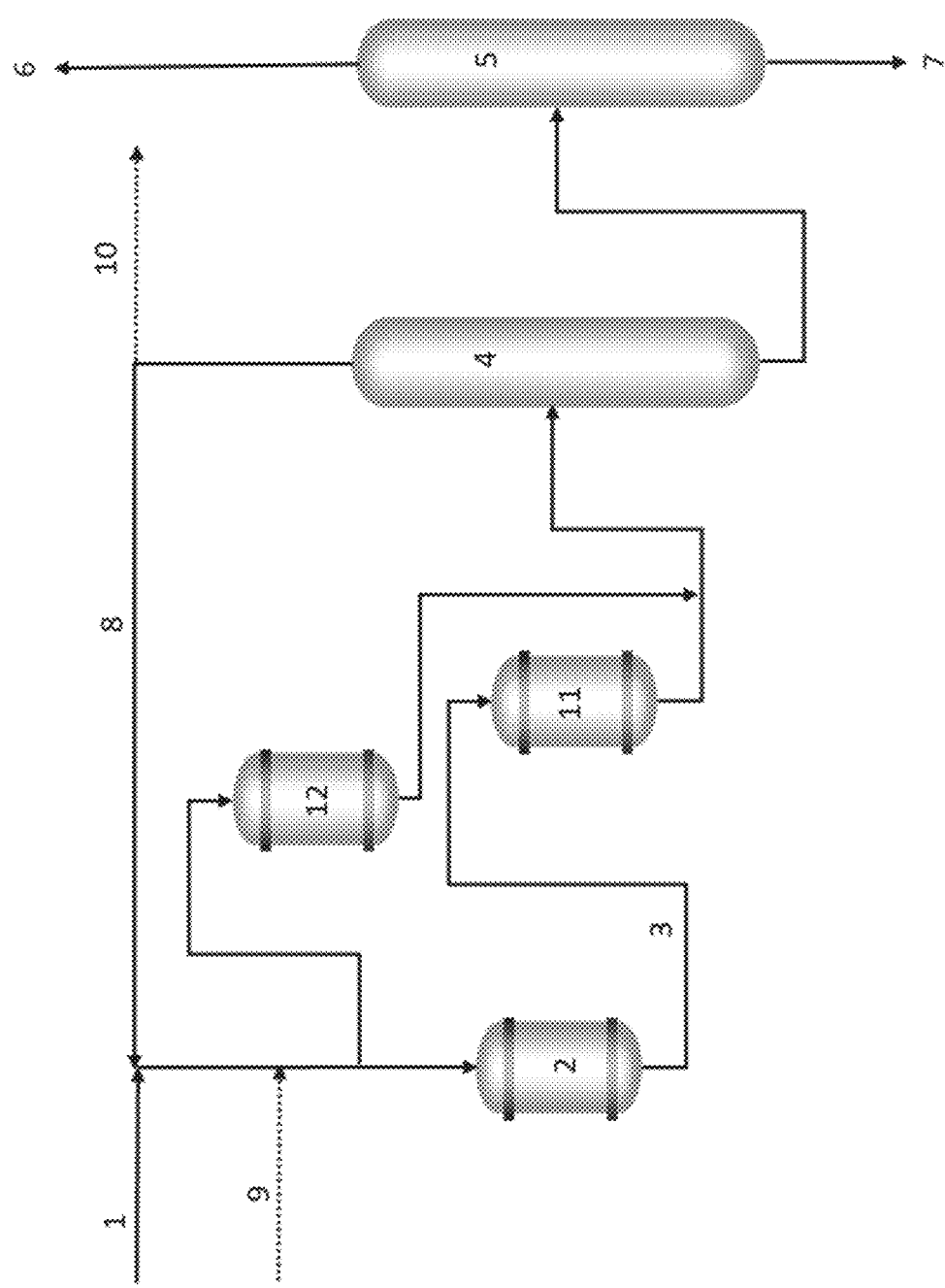
FIG. 4 shows an embodiment of the process according to the invention having 3 reactors (2, 11, 12), wherein in each case one reactor is connected in parallel and one reactor is connected in series relative to the first reactor.

FIG. 4 elucidates one embodiment of the present invention having 3 reactors (2, 11, 12), wherein in each case one reactor is connected in parallel and one reactor is connected in series relative to the first reactor. An isobutene-containing input stream composed of an isobutene-containing hydrocarbon stream (feed) (1) and a stream (recycle) (8) recirculated from the first distillation column (4) is passed to the first reactor (2) and to the second reactor (12) connected in parallel for oligomerization of the isobutene present. According to the invention, the ratio of recycle to feed in the isobutene-containing input stream is at least 4, preferably at least 5, particularly preferably at least 6. The discharge (3) from the first reactor (2) is passed to a third reactor (11) connected in series to oligomerize the remaining isobutene. In the first distillation column (4), the discharge from the third reactor (11) and the discharge from the second reactor (12), which are in each case a mixture of at least unconverted isobutene and isobutene oligomers, are then freed of low boilers (isobutene and optionally isobutane) which are withdrawn from the top of the distillation column (4) and recirculated to the first and the second reactor (2, 12). The sump product from the distillation column (4) consists substantially of diisobutene and higher oligomers which are separated from one another in the subsequent distillation column (5). The diisobutene (6) is obtained from the column top and the higher oligomers (7) accumulate in the sump. The figure also indicates two optional configurations, namely additional supply of inert alkanes (9) and discharging of a portion of the low boilers (10).

The invention claimed is:

1. A process for producing diisobutene comprising:
performing an oligomerization of isobutene in the absence of an oxygenate over an acid catalyst in at least one reaction stage which in each case contains at least one reactor and at least one distillation column,
wherein an isobutene-containing input stream, which comprises an isobutene-containing hydrocarbon stream as feed and a recirculated stream as recycle, is converted in the at least one reactor of the at least one reaction stage to obtain a product mixture containing at least the diisobutene formed having a proportion of 2,4,4-trimethylpent-1-ene of at least 75 mol %, and unconverted isobutene, and an obtained product mixture is supplied to the at least one distillation column,
wherein at the top of the distillation column a residual hydrocarbon stream depleted in the diisobutene formed based on the obtained product mixture is withdrawn and at least partially recirculated to the at least one reactor as recycle,
wherein a ratio of recycle to feed is at least 4, whereby the selectivity of the oligomerization is increased such that the diisobutene formed has said proportion of 2,4,4-trimethylpent-1-ene.

2. The process according to claim 1, wherein the ratio of recycle to feed is at least 5.

3. The process according to claim 2, wherein the ratio of recycle to feed is at least 6.

4. The process according to claim 1, wherein the isobutene-containing hydrocarbon stream is a $C_4$-hydrocarbon stream.

5. The process according to claim 1, wherein the isobutene-containing hydrocarbon stream is a pure isobutene stream.

6. The process according to claim 1, wherein the residual hydrocarbon stream withdrawn at the top of the distillation column is completely recirculated to the at least one reactor.

7. The process according to claim 1, wherein the at least one reaction stage comprises at least two reactors which are connected in series or parallel relative to one another.

8. The process according to claim 1, wherein the oligomerization is performed in a liquid phase.

9. The process according to claim 1, wherein the acid catalyst is an acidic ion exchange resin in which a portion of acidic protons have been exchanged for metal ions.

10. The process according to claim 9, wherein 0.1% to 70% of the acidic protons of the acidic ion exchange resin have been exchanged for metal ions.

11. The process according to claim 9, wherein the metal ions are ions of alkali metals, alkaline earth metals, and/or rare earths.

12. The process according to claim 1, wherein the at least one reactor is a flow reactor.

13. The process according to claim 1, wherein the at least one reactor is operated adiabatically, polytropically, or virtually isothermally using a coolant.

14. The process according to claim 1, wherein the oligomerization is performed at a temperature between 5° C. and 160° C.

15. The process according to claim 1, wherein a first reaction stage is run with a total feed of the is butene-containing input stream of at least 2.5 t per t of catalyst and hour (h) (unit t/(t*h)).

16. The process according to claim 1, wherein the product mixture containing at least the diisobutene formed has proportion of 2,4,4-trimethylpent-1-ene of at least 78 mol %.

17. The process according to claim 10, wherein 30% to 60% of the acidic protons of the acidic ion exchange resin have been exchanged for metal ions.

18. The process according to claim 12, wherein the flow reactor is a fixed bed reactor, a tube bundle reactor, a continuous stirred tank reactor, or a loop reactor.

19. The process according to claim 14, wherein the oligomerization is performed at a temperature between 40° C. and 90° C.

20. The process according to claim 15, wherein the first reaction stage is run with a total feed of the isobutene-containing input stream of at least 3.5 t per t of catalyst and hour (h).

* * * * *